United States Patent
Bennett et al.

(10) Patent No.: US 9,359,394 B2
(45) Date of Patent: Jun. 7, 2016

(54) STEREOSELECTIVE GLYCOSYLATION REACTIONS

(71) Applicant: Trustees of Tufts College, Boston, MA (US)

(72) Inventors: Clay S. Bennett, Somerville, MA (US); An-Hsiang A. Chu, Somerville, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 14/247,729

(22) Filed: Apr. 8, 2014

(65) Prior Publication Data

US 2014/0303359 A1     Oct. 9, 2014

Related U.S. Application Data

(60) Provisional application No. 61/809,590, filed on Apr. 8, 2013.

(51) Int. Cl.

| | |
|---|---|
| C07H 15/207 | (2006.01) |
| C07H 19/01 | (2006.01) |
| C07H 3/04 | (2006.01) |
| C07H 3/06 | (2006.01) |
| C07J 17/00 | (2006.01) |
| C07H 15/18 | (2006.01) |
| C07H 15/203 | (2006.01) |
| C07H 15/24 | (2006.01) |

(52) U.S. Cl.
CPC .............. *C07J 17/005* (2013.01); *C07H 15/18* (2013.01); *C07H 15/203* (2013.01); *C07H 15/24* (2013.01); *Y02P 20/55* (2015.11)

(58) Field of Classification Search
None
See application file for complete search history.

(56) References Cited

U.S. PATENT DOCUMENTS

2011/0009612 A1    1/2011   Pohl et al.

FOREIGN PATENT DOCUMENTS

| WO | WO-2007/091040 A2 | 8/2007 |
|---|---|---|
| WO | WO-2011/137181 A1 | 11/2011 |
| WO | WO-2011/149778 A1 | 12/2011 |
| WO | WO-2012/082635 A1 | 6/2012 |

OTHER PUBLICATIONS

Van Well, Journal of Carbohydrate Chemistry, 24:463-474, 2005.*
Qin, Carbohydrate Research 403 (2015) 104-114.*
Gu, J. Org. Chem. 2014, 79, 1100-1110.*
Chu, Organic Letters 2013, vol. 15, No. 10, 2566-2569, supporting information.*
Bennett C.S., "Highly stereoselective glycosylation reactions using shelf-stable donors: Towards glycosylation as an $S_N2$ reaction.", PowerPoint presentation to University of Massachusetts Dartmouth, Mar. 6, 2013.
Boonyarattanakalin, S. et al., Chemical synthesis of all phosphatidylinositol mannoside (PIM) glycans from Mycobacterium tuberculosis, *J. Am. Chem. Soc.*, 130(49):16791-16799 (2008).
Chu, A. H. et al., "Selective Synthesis of 1,2-cis-α-Glycosides Without Directing Groups. Application to Iterative Oligosaccharide Synthesis", *Org. Lett.*, 15(10):2566-2599 (2013).
Cox, D. J. et al., "Glycosylation Catalyzed by a Chiral Brønsted Acid", *Org. Lett.*, 12(7):1452-1455 (2010).
Dieskau, A. P. et al., "A Mild Ligand-Free Iron-Catalyzed Liberation of Alcohols from Allylcarbonates", *Org. Lett.*, 13(20):5544-5547 (2011).
Garcia, B. A. et al., "Dehydrative Glycosylation with Activated Diphenyl Sulfonium Reagents. Scope, Mode of C(1)-Hemiacetal Activation, and Detection of Reactive Glycosyl Intermediates", *J. Am. Chem. Soc.*, 122:4269-4279 (2000).
Kaeothip, S. et al., "Unexpected Orthogonality of S-Benzoxazolyl and S-Thiazolinyl Glycosides: Application to Expeditious Oligosaccharide Assembly", *Org. Lett.*, 11(4):799-802 (2009).
Koshiba, M. et al., "Catalytic Stereoselective Glycosidation with Glycosyl Diphenyl Phosphates: Rapid Construction of 1,2-cis-α-Glycosidic Linkages", *Chem. Asian J.*, 3:1664-1677 (2008).
Matwiejuk, M. et al., "New Method for Regioselective Glycosylation Employing Saccharide Oxyanions", *Eur. J. Org. Chem.*, 29:5860-5878 (2011).
Nguyen, H. M. et al., "Sulfide-Mediated Dehydrative Glycosylation", *J. Am. Chem. Soc.*, 123(36):8766-8772 (2001).
Ren, C.-T. et al., "Synthesis of a Tetrasaccharide Glycosyl Glycerol. Precursor to Glycolipids of *Meiothermus taiwanensis* ATCC BAA-400", *J. Org. Chem.*, 72(14):5427-5430 (2007).
Shingu, Y. et al., "An easy access to halide ion-catalytic α-glycosylation using carbon tetrabromide and triphenylphosphine as multifunctional reagents", *Org. Biomol. Chem.*, 1:2518-2521 (2003).
Tani, S. et al., "A novel method for regioselective ring-opening reduction of 4,6-O-benzylidene hexopyranoside derivatives using $CoCl_2$ and $BH_3 \cdot THF$", *Tetrahedron Lett.*, 48(17):3101-3104 (2007).

(Continued)

*Primary Examiner* — Layla Berry
(74) *Attorney, Agent, or Firm* — Dana M. Gordon; Foley Hoag LLP (57) ABSTRACT

Disclosed is a method for selective synthesis of 1,2-cis-α-linked glycosides which does not require the use of the specialized protecting group patterns normally employed to control diastereoselectivity. Thioglycoside acceptors can be used, permitting iterative oligosaccharide synthesis. The approach eliminates the need for lengthy syntheses of monosaccharides possessing highly specialized and unconventional protecting group patterns.

14 Claims, 2 Drawing Sheets

(56) References Cited

OTHER PUBLICATIONS

Xiong, D.-C., et al., "Bromodimethylsulfonium Bromide-Silver Triflate: A New Powerful Promoter System for the Activation of Thioglycosides", *Adv. Synth. Catal.*, 350:1696-1700 (2008).

Xue, J. et al., "Synthetic Studies on the Carbohydrate Moiety of Amipurimycin", *J. Carbohydr. Chem.*, 27:51-69 (2008).

* cited by examiner

STEREOSELECTIVE GLYCOSYLATION REACTIONS

RELATED APPLICATION

This application claims the benefit under 35 U.S.C. §1.119 (e) of U.S. Provisional Application No. 61/809,590, filed Apr. 8, 2013.

GOVERNMENT SUPPORT

This invention was made with government support under grant 1300334 awarded by the National Science Foundation. The government has certain rights in the invention.

BACKGROUND OF THE INVENTION

Oligosaccharides are arguably the most abundant and complex biopolymers found in nature. It has been estimated that the information capacity of these molecules is staggering,[1] and it is well recognized that they play a critical role in a variety of biological processes.[2] In addition, unusual glycosylation patterns associated with cancer and many pathogens have prompted increasing interest in the development of carbohydrate-based vaccines.[3] Despite their obvious importance, our understanding of the molecular basis of oligosaccharide function lags far behind that of genomics and proteomics. This is due in large part to the difficulties associated with obtaining homogenous material for study. Since biological sources produce oligosaccharides as complex heterogeneous mixtures, chemical and chemoenzymatic synthesis are the only means of producing homogenous material. While the past few decades have seen enormous progress in the synthesis of complex oligosaccharides,[4] the construction of novel structures is still a daunting task. This is especially true if the sequence in question contains so-called difficult linkages, where it is extremely challenging to control anomeric stereochemistry during glycosylation. As a result of these factors, there has been renewed interest in oligosaccharide synthesis, and calls for the development of new glycosylation protocols that provide reliable control over anomeric stereochemistry.[5]

Most chemical glycosylation reactions proceed through an $S_N1$-type mechanism. Directing groups are therefore frequently necessary to control selectivity. This leads to long synthetic sequences to prepare a polysaccharide of interest.

Oligosaccharides found on the surface of pathogens and malignant cells frequently possess 1,2-cis-α-linked glycosides as a key structural element.[3a] Often these structures are distinct from mammalian oligosaccharides. The possibility of using these structures in carbohydrate-based vaccine candidates has promoted numerous investigations into the construction of these linkages.[4]

Unfortunately, however, 1,2-cis-α-linked glycosides are among the most difficult glycosidic linkages to synthesize. Many of the approaches developed to construct these linkages rely on the use of unconventional protecting groups to control selectivity.[6-9] Alternatively, it is possible to obtain selectivity in the absence of directing groups by using leaving groups that undergo $S_N2$-like displacement.[10,11] For example, glycosyl iodides undergo glycosylation in the presence of excess iodide ion to form products with high a-selectivity.[12,13] These species are unstable, however, and must be generated under harsh conditions. This limits their utility both with sensitive substrates, and with technologies such as iterative and one-pot oligosaccharide synthesis.[14,15]

SUMMARY OF THE INVENTION

The invention provides methods of performing highly selective (e.g., >14:1 α:β) glycosylation reactions in the absence of directing groups. In certain embodiments, the methods involve in situ conversion of a stable donor, such as a thioglycoside, into a reactive glycosyl iodide under mild conditions.[16-19] In accordance with the invention, it is now possible to synthesize 1,2-cis-α-linked glycoside linkages without the need to rely on the use of unconventional protecting groups to control selectivity.[6-9] In addition, the methods of the invention employ mild conditions and are amenable to pre-activation protocols, thereby permitting the use not only of sensitive substrates but also of iterative and one-pot oligosaccharide synthesis. The yields achieved through this chemistry are also favorable.

An aspect of the invention is a method of forming a glycosidic bond, comprising:

combining a glycosyl sulfide, a sulfoxide, molecular sieves, and a non-nucleophilic base, thereby forming a first reaction mixture;

combining a sulfonic anhydride and the first reaction mixture, thereby forming a second reaction mixture;

combining tetrabutylammonium iodide (TBAI) and the second reaction mixture, thereby forming a third reaction mixture; and combining a glycosyl acceptor and the third reaction mixture, thereby forming a glycosidic bond;

wherein the glycosidic bond is formed with greater than or equal to 90% stereoselectivity for a particular stereochemical configuration.

DETAILED DESCRIPTION OF THE INVENTION

Figure 1:
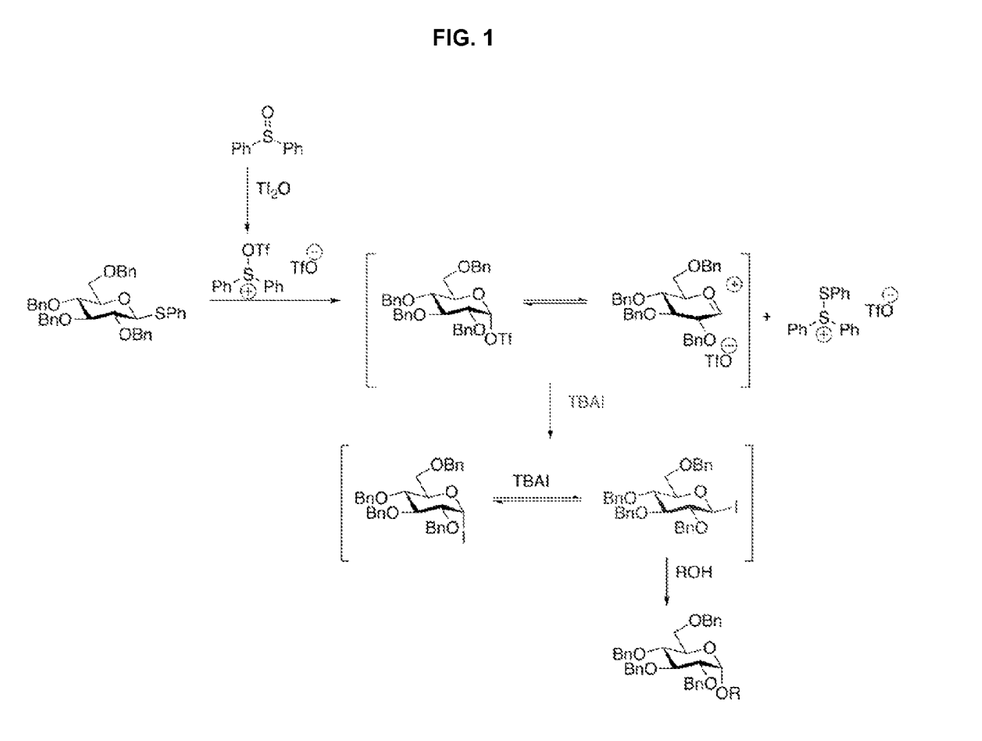
FIG. 1 is a scheme depicting certain features of the invention.
Figure 2:
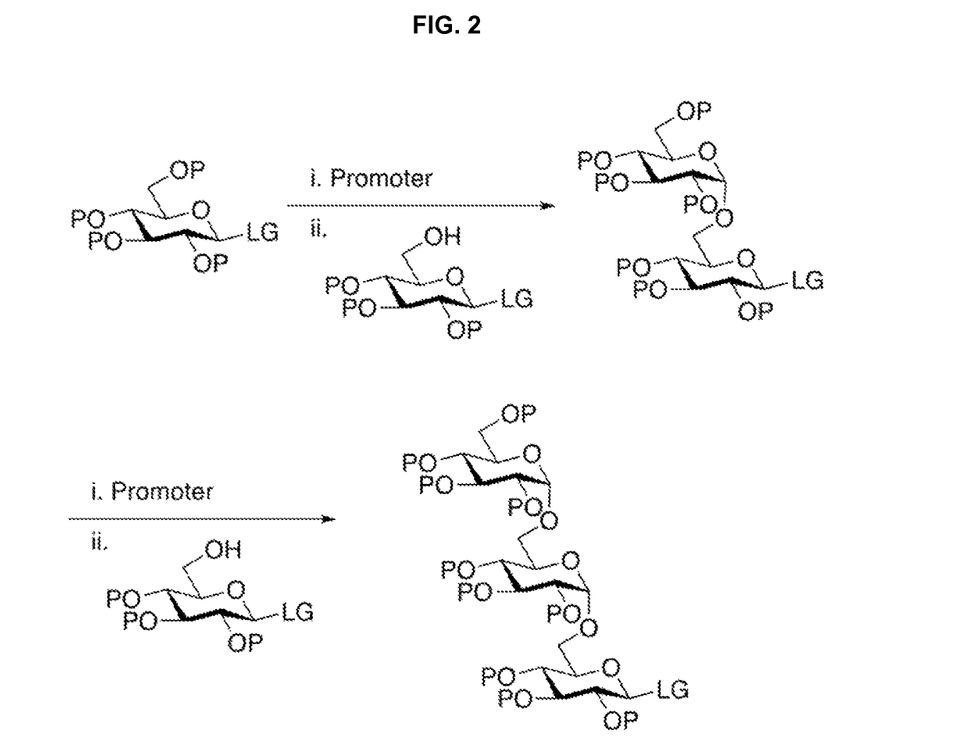
FIG. 2 is a scheme depicting iterative synthesis without the need for protecting group (PG) manipulations and donor activation between each glycosylation step.

Thioglycosides are particularly useful for iterative and one-pot synthesis. Many methods for thioglycoside activation involve in situ generation of a glycosyl triflate. We reasoned that this intermediate could be trapped by iodide ion, thereby providing mild conditions for the in situ formation of a glycosyl iodide for 1,2-cis-α-selective glycosylation reactions.

Preliminary studies involved activating thioglycoside 1 with $Ph_2SO$/trifluoromethanesulfonic anhydride ($Tf_2O$) in the presence of the non-nucleophilic base tri-tert-butylpyrimidine (TTBP), followed by addition of excess tetrabutylammonium iodide (TBAI). After stirring at −78° C. for 10 min, the reaction was treated with cholesterol (2) as a nucleophilic acceptor and allowed to warm to room temperature. The presence of TBAI led to a reversal of selectivity from that observed using $Ph_2SO$/$Tf_2O$ alone (Table 1, entries 2 vs. 1). Addition of the nucleophile in 1,4-dioxane led to a modest increase in selectivity, accompanied by a loss in yield (Table 1, entry 4). Further experiments revealed that both the yield and selectivity could be improved through the use of 4 Å (Angstrom) molecular sieve (MS) (entry 5). To determine if the selectivity of the reaction was due chiefly to the ethereal solvent, we ran the reaction with 1,4-dioxane in the absence of TBAI. Under these conditions the reaction was non-selective (1:1.2 α:β, Table 1, entry 8), clearly indicating the importance of iodide for the reaction. This last result supports the idea that the conditions are promoting the in situ conversion of the thioglycoside into the corresponding glycosyl iodide. Since TTBP suppresses in situ anomerization of glycosylation products, the α-selectivity observed in entry 5 is the result of this glycosyl iodide reacting under halide ion conditions.

TABLE 1

Preliminary Reaction Optimization

| entry | TBAI (equiv) | solvent | sieves | yield (%) | α:β |
|---|---|---|---|---|---|
| 1 | 0 | $CH_2Cl_2$ | — | 85 | 1:3 |
| 2 | 3 | $CH_2Cl_2$ | — | 68 | 2.5:1 |
| 3 | 3 | $Et_2O$ | — | 62 | 3.3:1 |
| 4 | 3 | 1,4-dioxane | — | 58 | 5.2:1 |
| 5 | 3 | 1,4-dioxane | 4 Å | 83 | 7.7:1 |
| 6 | 3 | THF | 4 Å | 62 | 7.1:1 |
| 7 | 3 | 1,4-dioxane | 5 Å | 75 | 6.6:1 |
| 8 | 0 | 1,4-dioxane | 4 Å | 56 | 1:1.2 |
| 9[a] | 3 | 1,4-dioxane | 4 Å | 70 | 1.3:1 |

[a] 1-benzenesulfinyl piperidine used in place of $Ph_2SO$.

Selectivity also appeared to depend on the nature of the thiophilic promoter; 1-benzenesulfinyl piperidine (BSP)/$Tf_2O$ led to a loss of selectivity (Table 1, entry 9). While the reason for this diminished selectivity is not known, we surmise that it may be due to the inability of this latter promoter to completely convert the thioglycoside to a glycosyl triflate at low temperature. If activation occurs upon warming, the acceptor is already present in the reaction and can react with the glycosyl triflate intermediate, leading to a loss of selectivity.

Under the optimal conditions described above, the reaction of 1 with sugar acceptor 4 led to the formation of disaccharide 5 accompanied by what appeared to be unreacted donor (Table 2, entry 1). This was surprising, since we had observed that the thioglycoside 1 was rapidly consumed upon activation with $Ph_2SO/Tf_2O$. We reasoned that the donor was somehow being regenerated under the reaction conditions following activation. To determine what was occurring, we examined the reaction in the absence of an acceptor. Under these conditions we found that 1 was quickly consumed upon activation with $Ph_2SO/Tf_2O$; however, it slowly formed again after the addition of TBAI. To confirm that TBAI was leading to regeneration of the donor, we examined the effect of TBAI stoichiometry on the yield of the reaction with 4. The addition of 2 equivalents of TBAI led to an increase in yield (89%) accompanied by a loss in selectivity, while the addition of 5 equivalents afforded the desired product as a single anomer, albeit in reduced yield (Table 2, entries 2 and 3).

TABLE 2

Effect of TBAI and N-methylmaleimide.

| entry | TBAI (equiv) | additive (equiv) | yield (%) | α:β |
|---|---|---|---|---|
| 1 | 3 | — | 72 | 11:1 |
| 2 | 2 | — | 89 | 4:1 |
| 3 | 5 | — | 62 | α only |
| 4 | 5 | N-methyl-malimide (1.5 equiv) | 87 | 18:1 |

Based on these results we concluded that TBAI was reacting with the by-product of thioglycoside activation (6) to generate phenylthiolate 7 (Scheme 1). Compound 7 then effectively competed with the acceptor to regenerate the donor, which, in the absence of additional promoter, was now inert under the reaction conditions. Rationalizing that a thiol scavenger could remove 7 from the reaction, and thereby permit the use of the excess TBAI necessary for selectivity, we chose to examine the effect of N-methylmaleimide on the reaction. To this end, activation of 1 in the presence of N-methylmaleimide, followed first by the addition of 5 equivalents TBAI, then 4 in dioxane, led to the formation of 5 in 87% yield with excellent selectivity (18:1 α:β, Table 2, entry 4). We therefore adopted these conditions for the remainder of this study.

Scheme 1. Possible Mechanism of Thioglycoside Regeneration.

The scope of the reaction was next examined with a number of sugar acceptors (Table 3). Both glucose and galactose donors reacted with a number of acceptors to provide products with excellent selectivity. This included a re-examination of cholesterol as a model small molecule acceptor, which showed that these modifications led to a dramatic increase in selectivity over our initial conditions (Table 3, entries 1 and 2 vs. Table 1, entry 5). In the case of more hindered acceptors, it was necessary to use 3 equivalents of N-methylmaleimide to obtain good yields (Table 3, entries 8 and 9). Even under these conditions, the use of the hindered acceptor 11 provided the product in lower yield than observed with other acceptors (Table 3, entry 10), and the reaction was again accompanied by regeneration of the donor. Products 3 and 12-20 are described in the Examples section.

TABLE 3

Reaction Scope.

| entry | donor | acceptor | product | time (h) | yield (%) | α:β |
|---|---|---|---|---|---|---|
| 1 | 1a | 2 | 3 | 18 | 75 | 20:1 |
| 2 | 1b | 2 | 12 | 18 | 76 | 30:1 |
| 3 | 1b | 4 | 13 | 18 | 81 | α only |
| 4 | 1a | 8 | 14 | 18 | 57 | 16:1 |

TABLE 3-continued

| | | | | | | |
|---|---|---|---|---|---|---|
| 5 | 1b | 8 | 15 | 18 | 58 | α only |
| 6 | 1a | 9 | 16 | 18 | 79 | 20:1 |
| 7 | 1b | 9 | 17 | 18 | 81 | α only |
| 8[a] | 1a | 10 | 18 | 40 | 59 | 19:1 |
| 9[a] | 1b | 10 | 19 | 40 | 70 | 20:1 |
| 10[a] | 1a | 11 | 20 | 64 | 41 | α only |

[a]3 equiv N-methylmaleimide used.
"α only" denotes only α detected.

Our observation that the thioglycoside that was regenerated upon addition of TBAI was not a competent donor prompted us to examine thioglycoside acceptors in the reaction. If thioglycoside acceptors could be used successfully, it would expand the reaction's utility by permitting iterative and, potentially, one-pot oligosaccharide synthesis. As a preliminary study, we examined the reaction between 1 and acceptor 21. Under our conditions, the anomeric sulfide in acceptor 21 was not activated, and we were able to obtain disaccharide 22 in good yield and excellent selectivity (Scheme 2). This product was then used directly as a donor in a reaction with acceptor 4 to afford 23. Interestingly, the stoichiometry of the donor and acceptor did not appear to affect the reaction. Using either the donor or acceptor in excess led to the formation of 23 in excellent selectivity (>20:1 α:β). Heating the reaction after it was warmed to room temperature resulted in an increase in yield, with a slight decrease in selectivity (14:1 α:β). The loss in selectivity could be explained by invoking a glycosyl iodide intermediate reacting in the presence of excess iodide ion. Specifically, at room temperature the glycosyl donor exists as a mixture of α- and β-iodides, with the β-iodide being significantly more reactive. At higher temperatures the α-iodide becomes a more competent donor, leading to a slight erosion of selectivity. Despite this, at higher temperatures the reaction still afforded the product in synthetically useful selectivities. More importantly, the results open up the exciting possibility that this approach could ultimately be utilized for stereoselective one-pot oligosaccharide synthesis, using pre-activation protocols.

Scheme 2. Iterative Oligosaccharide Synthesis.

| donor:<br>acceptor | time<br>(h) | t (° C.) | yield (%) | α:β |
|---|---|---|---|---|
| 1:2 | 64 | 25 | 30 | 22:1 |
| 2:1 | 64 | 25 | 35 | 20:1 |
| 1:2 | 18 | 80 | 42 | 14:1 |

Remarkably, we have shown that activating thioglycosides with $Ph_2SO/Tf_2O$ followed by TBAI leads to the in situ formation of a species that undergoes glycosylation to afford 1,2-cis-α-glycosides in good yield and excellent selectivity without the need for directing groups. The dependence of selectivity on the quantity of TBAI in the reaction indicates that the reaction may be proceeding through a glycosyl iodide intermediate. Excess TBAI can lead to regeneration of the starting donor; however, this can be suppressed with the addition of N-methylmaleimide as a thiol scavenger. The fact that the regenerated donor is unreactive prompted us to examine thioglycoside acceptors in the reaction. These latter acceptors can be used without detrimental effects, permitting iterative oligosaccharide synthesis. This approach will significantly facilitate oligosaccharide synthesis by eliminating the need to use highly specialized protecting group patterns on monosaccharide coupling partners, or unstable glycosyl donors in the construction of 1,2-cis-α-glycosides.

Exemplary Methods of the Invention

An aspect of the invention is a method of forming a glycosidic bond, comprising:

combining a glycosyl sulfide, a sulfoxide, molecular sieves, and a non-nucleophilic base, thereby forming a first reaction mixture;

combining a sulfonic anhydride and the first reaction mixture, thereby forming a second reaction mixture;

combining tetrabutylammonium iodide (TBAI) and the second reaction mixture, thereby forming a third reaction mixture; and combining a glycosyl acceptor and the third reaction mixture, thereby forming a glycosidic bond;

wherein the glycosidic bond is formed with greater than or equal to 90% stereoselectivity for a particular stereochemical configuration.

In an embodiment, the glycosidic bond is formed with greater than or equal to 95% stereoselectivity for a particular stereochemical configuration.

In an embodiment, the glycosidic bond is formed with greater than or equal to 96% stereoselectivity for a particular stereochemical configuration.

In an embodiment, the glycosidic bond is formed with greater than or equal to 97% stereoselectivity for a particular stereochemical configuration.

In an embodiment, the glycosidic bond is formed with greater than or equal to 98% stereoselectivity for a particular stereochemical configuration.

In an embodiment, the glycosidic bond is formed with greater than or equal to 99% stereoselectivity for a particular stereochemical configuration.

In an embodiment in accordance with any of the foregoing, the particular stereochemical configuration is an α linkage.

In an embodiment in accordance with any of the foregoing, the glycosyl sulfide is a glycosyl phenyl sulfide.

In an embodiment in accordance with any of the foregoing, the molecular sieves are 4 Angstrom molecular sieves.

In an embodiment in accordance with any of the foregoing, the sulfoxide is phenyl sulfoxide ($Ph_2SO$).

In an embodiment in accordance with any of the foregoing, the sulfonic anhydride is trifluoromethanesulfonic anhydride.

In an embodiment in accordance with any of the foregoing, the non-nucleophilic base is selected from the group consisting of tri-tert-butylpyrimidine (TTBP), 2,6-di-tert-butylpyridine, N,N-diisopropylethylamine (DIPEA), 1,8-diazabicycloundec-7-ene (DBU), 2,6-lutidine, 2,4,6-collidine, tert-butyl-phosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide.

In an embodiment in accordance with any of the foregoing, the non-nucleophilic base is tri-tert-butylpyrimidine (TTBP).

In an embodiment in accordance with any of the foregoing, the glycosyl sulfide is selected from the group consisting of In an embodiment in accordance with any of the foregoing, the glycosyl acceptor comprises an alcohol, a thiol, or an amine.

In an embodiment in accordance with any of the foregoing, the glycosyl acceptor is a monosaccharide, a disaccharide, an oligosaccharide, or a polysaccharide, each comprising at least one —OH, —SH, or primary or secondary amino group.

In an embodiment in accordance with any of the foregoing, the glycosyl acceptor is selected from the group consisting of:

In an embodiment in accordance with any of the foregoing, the first reaction mixture further comprises a thiol scavenger.

In an embodiment in accordance with any of the foregoing, the thiol scavenger is a maleimide. In an embodiment in accordance with any of the foregoing, the thiol scavenger is N-methylmaleimide. In other embodiments, the thiol scavenger is N-ethylmaleimide (NEM) or S-methyl methanethiosulfonate (MMTS). Additional thiol scavengers (thiol trapping agents) are disclosed in, for example, Avonto, C. et al., *Angew Chem Int Ed Engl.* 50(2):467-71 (2011).

In an embodiment in accordance with any of the foregoing, the method further comprises the step of cooling the first reaction mixture to about −78° C.

In an embodiment in accordance with any of the foregoing, the TBAI is present in about 5-fold molar excess relative to the glycosyl sulfide.

EXAMPLES

The present invention is further illustrated by the following examples, which in no way should be construed as further limiting. The entire contents of all the references (including literature references, issued patents, published patent applications, and co-pending patent applications) cited throughout this application are hereby expressly incorporated by reference.

General Experimental Details

All reactions were performed under inert argon atmosphere. Flash column chromatography was performed on SiliCycle P-60 silica gel, 230-400 Mesh. Analytical and preparative thin layer chromatography was carried out on EMD silica gel 60 F-254 plates. Products were visualized using UV or by staining with 5% aqueous sulfuric acid or ceric ammonium molybdate. NMR spectra were recorded on a Bruker Avance III NMR spectrometer at 500 MHz for $^1$H-NMR and 125 MHz for $^{13}$C-NMR. Chemical shifts are reported in ppm relative to TMS (for $^1$H-NMR in CDCl$_3$) or CDCl$_3$ (for $^{13}$C-NMR in CDCl$_3$). For $^1$H NMR spectra, data are reported as follows: δ shift, multiplicity [s=singlet, m=multiplet, t=triplet, d=doublet, dd=doublet of doublets, ddd=doublet of doublet of doublets, dddd=doublet of doublet of doublet of doublets, dt=doublet of triplets, td=triplet of doublets, q=quartet], coupling constants are reported in Hz. Low resolution mass spectra (LRMS) were recorded using a Finnigan LTQ ESI-MS with an additional APCI source. High resolution mass spectra (HRMS) were obtained at Massachusetts Institute of Technology Department of Chemistry instrumentation facility using a peak-matching protocol to determine the mass and error range of the molecular ion. Optical rotations were measured on a Rudolph Research Analysis AUTOPUL IV polarimeter at 589 nm in a 5 cm cell at 24° C.

Materials

Prior to running the glycosylation reactions, all reagents, with the exception of trifluoromethanesulfonic anhydride (Tf$_2$O), were dried by repeated azeotropic removal of water using toluene and a rotary evaporator at <40° C. Solvents for reactions were dried on an Innovative Technologies PureSolv 400 solvent purifier. NMR solvents were purchased from Cambridge Isotope Labs. Molecular sieves (4 Å) for reactions were pulverized and flame dried immediately before use. Compound 1a, 1b[16], 4[17], 10[18], 11[19] and 21[20] were synthesized following literature procedures. Trifluoromethanesulfonic anhydride (Tf$_2$O) was purchased from Sigma-Aldrich and distilled freshly before use. All other chemicals were purchased at the highest possible purity from Sigma-Aldrich and used as received.

Example 1

Cholesteryl-O-2,3,4,6-tetra-O-benzyl-α-D-glucopyranose (3)

A solution of donor 1a (1.0 equiv., 0.075 mmol, 47.5 mg), Ph$_2$SO (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride (Tf$_2$O, 1.4 equiv., 0.106 mmol, 18 µL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which time the reaction mixture was treated with a solution of acceptor 2 (2.0 equiv., 0.150 mmol, 43.5 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous NaHCO$_3$. The organic layer was dried (Na$_2$SO$_4$), filtered and concentrated. The crude product was purified by silica gel flash column chromatography (5%→10% ethyl acetate in hexanes) to afford product 3 (0.056 mmol, 51.1 mg, 75% yield, 20:1 α:β), the spectroscopic data of which is in good agreement with those reported previously.[21]

$^1$H NMR (500 MHz, CDCl$_3$): δ 7.37-7.12 (m, 20H), 5.29 (s, 1H), 5.01 (d, J=10.9 Hz, 1H), 4.93 (d, J=4.0 Hz, 1H), 4.83 (d, J=10.9 Hz, 1H), 4.82 (d, J=10.9 Hz, 1H), 4.77 (d, J=12.0 Hz, 1H), 4.65 (d, J=12.0 Hz, 1H), 4.61 (d, J=12.0 Hz, 1H), 4.46 (d, J=10.9 Hz, 1H), 4.45 (d, J=12.0 Hz, 1H), 4.00 (t, J=9.2 Hz, 1H), 3.89-3.86 (m, 1H), 3.74 (dd, J=10.9, 3.4 Hz, 1H), 3.66-3.62 (m, 2H), 3.55 (dd, J=9.2, 4.0 Hz, 1H), 3.48 (m, 1H), 2.43 (m, 1H), 2.27 (m, 1H), 2.02 (m, 1H), 1.95 (m, 1H), 1.88-1.79 (m, 3H), 1.60-0.86 (m, 33H), 0.68 (s, 3H); $^{13}$C NMR (125 MHz, CDCl$_3$) δ 140.9, 139.1, 138.3, 138.1, 128.4, 128.3, 128.1, 127.9, 128.9, 127.8, 127.6, 127.5, 121.7, 94.7, 82.1, 80.0, 78.0, 76.7, 75.6, 75.1, 73.4, 73.0, 70.1, 68.8, 56.8, 56.2, 50.2, 42.3, 39.8, 39.5, 37.1, 36.8, 36.2, 35.7, 31.9, 29.6, 28.2, 27.9, 27.6, 24.3, 23.8, 22.8, 22.5, 21.1, 19.3, 18.7, 11.8.

Example 2

Methyl O-(2,3,4,6,-tetra-O-benzyl-α-D-glucopyranosyl)-(1->6)-2,3,4-tri-O-benzyl-α-D-glucopyranoside (5)

A solution of donor 1a (1.0 equiv., 0.075 mmol, 47.5 mg), Ph$_2$SO (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride (Tf$_2$O, 1.4 equiv., 0.106 mmol, 18 µL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 4 (2.0 equiv., 0.150 mmol, 69.6 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous NaHCO$_3$. The organic layer was dried (Na$_2$SO$_4$), filtered and concentrated. The crude product was purified by silica gel flash column chromatography (20%->30% ethyl acetate in hexanes) to afford product 5 (0.065 mmol, 64.3 mg, 87% yield, 18:1 α:β), the spectroscopic data of which is in good agreement with those reported previously.[22]

$^1$H NMR (500 MHz, CDCl$_3$): δ 7.32-7.12 (m, 35H), 4.98-4.92 (m, 4H), 4.83-4.76 (m, 3H), 4.71-4.63 (m, 4H), 4.58-4.55 (m, 3H), 4.47-4.40 (m, 2H), 3.99-3.94 (m, 2H), 3.82-3.77 (m, 3H), 3.72-3.70 (m, 1H), 3.65-3.60 (m, 3H), 3.56-3.54 (m, 2H), 3.44 (d, J=8.7 Hz, 1H), 3.35 (s, 3H); $^{13}$C NMR (125 MHz, CDCl$_3$) δ 139.0, 138.9, 138.6, 138.3, 138.1, 128.5, 128.4, 128.1, 128.0, 127.9, 127.8, 127.7, 127.6, 98.1, 97.4, 82.3, 81.8, 80.3, 80.1, 77.9, 77.7, 77.4, 75.8, 75.6, 75.1, 75.0, 73.5, 72.5, 70.5, 70.4, 68.6, 66.2, 55.3; LRMS (ESI, pos. ion) m/z: calcd. for $C_{62}H_{66}O_{11}Na$ (M+Na) 1009.46. found 1009.32.

Example 3

Cholesteryl-O-2,3,4,6-tetra-O-benzyl-α-D-galactopyranose (12)

A solution of donor 1b (1.0 equiv., 0.075 mmol, 47.5 mg), $Ph_2SO$ (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride ($Tf_2O$, 1.4 equiv., 0.106 mmol, 18 µL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 2 (2.0 equiv., 0.150 mmol, 43.5 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous $NaHCO_3$. The organic layer was dried ($Na_2SO_4$), filtered and concentrated. The crude product was purified by silica gel flash column chromatography (5%→10% ethyl acetate in hexanes) to afford product 12 (0.057 mmol, 51.8 mg, 76% yield, 30:1 α:β), the spectroscopic data of which is in good agreement with those reported previously.[27]

$^1$H NMR (500 MHz, $CDCl_3$): δ 7.37-7.25 (m, 20H), 5.25 (s, 1H), 4.99 (s, 1H), 4.97 (d, J=11.4 Hz, 1H), 4.85 (d, J=11.5 Hz, 1H), 4.79 (d, J=12.0 Hz, 1H), 4.73 (d, J=11.6 Hz, 1H), 4.67 (d, J=12.0 Hz, 1H), 4.57 (d, J=11.5 Hz, 1H), 4.47 (d, J=11.6 Hz, 1H), 4.40 (d, J=11.8 Hz, 1H), 4.08-4.00 (m, 2H), 3.98-3.94 (m, 2H), 3.53 (d, J=6.0 Hz, 2H), 3.51-3.43 (m, 1H), 2.44-2.39 (m, 1H), 2.28 (d, J=13.4 Hz, 1H), 2.00 (d, J=12.5 Hz, 1H), 1.94 (d, J=16.2 Hz, 1H), 1.90-1.79 (m, 3H), 1.61-0.87 (m, 33H), 0.68 (s, 3H); $^{13}$C NMR (125 MHz, $CDCl_3$) δ 140.9, 139.0, 138.8, 138.7, 138.1, 128.4, 128.3, 128.2, 128.0, 127.7, 127.6, 127.5, 127.4, 121.6, 95.6, 79.2, 75.3, 74.7, 73.4, 73.2, 69.3, 69.2, 56.8, 56.2, 50.2, 42.4, 40.0, 39.8, 39.6, 37.2, 36.8, 36.2, 35.8, 32.0, 31.9, 28.2, 28.0, 27.7, 24.3, 23.8, 22.8, 22.6, 21.1, 19.4, 18.7, 11.9.

Example 4

Methyl O-(2,3,4,6,-tetra-O-benzyl-α-D-galactopyranosyl)-(1->6)-2,3,4-tri-O-benzyl-α-D-glucopyranoside (13)

A solution of donor 1b (1.0 equiv., 0.075 mmol, 47.5 mg), $Ph_2SO$ (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride ($Tf_2O$, 1.4 equiv., 0.106 mmol, 18 µL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 4 (2.0 equiv., 0.150 mmol, 69.6 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous $NaHCO_3$. The organic layer was dried ($Na_2SO_4$), filtered and concentrated. The crude product was purified by silica gel flash column chromatography (20%→30% ethyl acetate in hexanes) to afford product 5 (0.060 mmol, 59.9 mg, 81% yield, α-only), the spectroscopic data of which is in good agreement with those reported previously.[26]

$^1$H NMR (500 MHz, $CDCl_3$): δ 7.37-7.18 (m, 35H), 4.99 (d, J=3.5 Hz, 1H), 4.96-4.92 (m, 2H), 4.84 (d, J=11.0 Hz, 1H), 4.80-4.78 (m, 2H), 4.74-4.68 (m, 4H), 4.59-4.65 (m, 2H), 4.54 (d, J=5.2 Hz, 1H), 4.52 (d, J=3.51 Hz, 1H), 4.43 (d, J=11.8 Hz, 1H), 4.37 (d, J=11.8 Hz, 1H), 4.02 (dd, J=5.9, 3.4 Hz, 1H), 3.98-3.88 (m, 4H), 3.80-371 (m, 3H), 3.58 (t, J=9.2 Hz, 1H), 3.53-3.47 (m, 2H), 3.40 (dd, J=6.1, 3.5 Hz, 1H), 3.29 (s, 3H); $^{13}$C NMR (125 MHz, $CDCl_3$) δ 138.9, 138.8, 138.5, 138.3, 138.1, 128.4, 128.3, 128.2, 128.1, 128.0, 127.9, 127.8, 127.7, 127.6, 127.5, 127.4, 127.3, 98.0, 97.9, 82.1, 80.2, 78.3, 78.0, 75.7, 75.2, 75.0, 74.8, 73.4, 73.3, 72.8, 72.5, 70.3, 69.4, 69.0, 66.4, 55.0.

75.1, 74.9, 73.6, 73.5, 72.9, 70.8, 69.9, 68.3, 67.3, 54.4, 28.3; LRMS (ESI, pos. ion) m/z: calcd. for $C_{49}H_{55}NO_{10}Na$ (M+Na) 840.38. found 840.23; HRMS (ESI, pos. ion) m/z: calcd. for $C_{49}H_{55}NO_{10}Na$ (M+Na) 840.3826. found 840.3718.

Example 5

14α

O-(3,4,6-tri-O-benzyl-α-D-glucopyranosyl)-N-(tert-butoxycarbonyl)-L-serine benzyl ester (14)

A solution of donor 1a (1.0 equiv., 0.075 mmol, 47.5 mg), Ph₂SO (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride (Tf₂O, 1.4 equiv., 0.106 mmol, 18 μL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 8 (2.0 equiv., 0.150 mmol, 44.3 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous NaHCO₃. The organic layer was dried (Na₂SO₄), filtered and concentrated. The crude product was purified by silica gel flash column chromatography (20% ethyl acetate in hexanes) to afford product 14 (0.043 mmol, 34.9 mg, 57% yield, 16:1 α:β).

$[\alpha]_D$=+0.166 (c=0.016, CH₂Cl₂); ¹H NMR (500 MHz, CDCl₃): δ 7.37-7.12 (m, 25H), 5.65 (d, J=8.5 Hz, 1H), 5.13-5.07 (m, 2H), 4.92 (d, J=10.8 Hz, 1H), 4.79 (dd, J=13.8, 11 Hz, 2H), 4.74 (d, J=2.7 Hz, 1H), 4.67-5.55 (m, 3H), 4.51-4.43 (m, 3H), 4.10 (d, J=10.5 Hz, 1H), 3.87 (t, J=9.3 Hz, 1H), 3.83 (dd, J=10.7, 2.6 Hz, 1H), 3.73-3.71 (m, 2H), 3.66-3.62 (m, 2H), 3.52 (dd, J=9.6, 3.3 Hz, 1H), 1.43 (s, 9H); ¹³C NMR (125 MHz, CDCl₃) δ 170.3, 155.5, 138.8, 138.2, 138.2, 137.9, 135.3, 98.5, 81.7, 80.0, 79.9, 77.7, 77.4, 77.3, 77.0, 76.7, 75.6,

15α

Example 6

O-(3,4,6-tri-O-benzyl-α-D-galactopyranosyl)-N-(tert-butoxycarbonyl)-L-serine benzyl ester (15)

A solution of donor 1b (1.0 equiv., 0.075 mmol, 47.5 mg), Ph₂SO (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride (Tf₂O, 1.4 equiv., 0.106 mmol, 18 μL). After stirring at low temperature for 5 min, a solution of tetrabutylammonium iodide (TBAI, 5 equiv., 0.375 mmol, 138 mg) in dichloromethane (0.75 mL) was added to the reaction. Stirring was continued for an additional 10 min at −78° C., after which the reaction mixture was treated with a solution of acceptor 8 (2.0 equiv., 0.150 mmol, 44.3 mg) in 1:1 dichloromethane/dioxane (0.50 mL/0.50 mL). The reaction mixture was then allowed to slowly warm up to room temperature and stirred for 18 h. The reaction was then first filtered with Celite and washed twice with saturated aqueous NaHCO₃. Pooled organic layer was dried (Na₂SO₄), filtered and concentrated, the crude product was purified by silica gel flash column chromatography (20% ethyl acetate in hexanes) to afford product 15 (0.044 mmol, 35.5 mg, 58% yield, α-only).

¹H NMR (500 MHz, C₆D₆): δ 7.34-7.31 (m, 7H), 7.27-7.25 (m, 2H), 7.21-6.97 (m, 16H), 6.09 (d, J=8.65 Hz, 1H), 5.02 (d, J=9.2 Hz, 1H), 5.00 (d, J=7.9 Hz, 1H), 9.90 (d, J=12.5 Hz, 1H), 4.75 (d, J=3.6 Hz, 1H), 4.68-4.64 (m, 1H), 4.58 (d, J=11.8 Hz, 1H), 4.55 (d, J=11.3 Hz, 1H), 4.50-4.46 (m, 2H), 4.41 (d, J=11.8 Hz, 1H), 4.36-4.33 (m, 2H), 4.14 (dd, J=9.7, 3.5 Hz, 1H), 4.10 (t, J=6.5 Hz, 1H), 3.99 (dd, J=11.0, 3.4 Hz, 1H), 3.85-3.83 (m, 2H), 3.76-3.75 (m, 2H), 3.72 (dd, J=8.3, 2.8 Hz, 1H), 1.43 (s, 9H); ¹³C NMR (125 MHz, CDCl₃) δ 170.4, 155.6, 138.8, 138.6, 138.0, 135.5, 128.5, 128.4, 128.3, 128.2, 128.1, 127.8, 127.7, 127.6, 127.5, 127.4, 99.36, 79.9, 78.7, 76.4, 74.5, 73.5, 73.2, 73.1, 70.4, 69.8, 68.7, 67.1, 54.5, 28.3; HRMS (ESI, pos. ion) m/z: calcd. for $C_{49}H_{55}NO_{10}Na$ (M+Na) 840.3899. found 840.3882.

Example 7

O-(2,3,4,6-tetra-O-benzyl-α-D-glucopyranosyl)-(1→6)-1,2;3,4-di-O-isopropylidene-α-D-galactopyranoside (16)

A solution of donor 1a (1.0 equiv., 0.075 mmol, 47.5 mg), $Ph_2SO$ (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride ($Tf_2O$, 1.4 equiv., 0.106 mmol, 18 μL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 9 (2.0 equiv., 0.150 mmol, 39.0 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous $NaHCO_3$. The organic layer was dried ($Na_2SO_4$), filtered and concentrated. The crude product was purified by silica gel flash column chromatography (20%→30% ethyl acetate in hexanes) to afford product 16 (0.059 mmol, 46.2 mg, 79% yield, 20:1 α:β), the spectroscopic data of which is in good agreement with those reported previously.[21]

$^1$H NMR (500 MHz, $CDCl_3$): δ 7.38-7.13 (m, 20H), 5.52 (d, J=5.2 Hz, 1H), 5.00 (d, J=4.0 Hz, 1H), 4.98 (d, J=10.9 Hz, 1H), 4.83 (d, J=10.9 Hz, 1H), 4.80 (d, J=10.9 Hz, 1H), 4.75 (d, J=12.0 Hz, 1H), 4.70 (d, J=12.0 Hz, 1H), 4.63 (d, J=12.0 Hz, 1H), 4.60 (dd, J=8.0, 2.3 Hz, 1H), 4.48 (d, J=10.9 Hz, 1H), 4.47 (d, J=12.0 Hz), 4.36 (dd, J=2.3, 8.0 Hz, 1H), 4.32 (dd, J=5.2, 2.3 Hz, 1H), 4.05 (m, 1H), 3.99 (t, J=9.7 Hz, 1H), 3.83 (m, 1H), 3.73-3.80 (m, 3H), 3.69 (t, J=9.7 Hz, 1H), 3.65 (dd, J=1.7, 10.3 Hz, 1H), 3.59 (dd, J=4.0, 9.7 Hz, 1H), 1.54 (s, 3H), 1.46 (s, 3H), 1.32 (s, 6H); $^{13}$C NMR (125 MHz, $CDCl_3$) δ 138.9, 138.4, 138.0, 128.6-126.6, 109.2, 108.6, 97.0, 96.9, 96.3, 81.8, 79.8, 77.6, 75.6, 74.9, 73.5, 72.3, 70.8, 70.7, 70.5, 68.4, 66.2, 65.7, 26.2, 26.1, 24.9, 24.7; LRMS (ESI, pos. ion) m/z: calcd. for $C_{46}H_{54}O_{11}$ (M+Na) 805.37. found 805.36.

Example 8

O-(2,3,4,6-tetra-O-benzyl-α-D-galactopyranosyl)-(1→6)-1,2;3,4-di-O-isopropylidene-α-D-galactopyranoside (17)

A solution of donor 1b (1.0 equiv., 0.075 mmol, 47.5 mg), $Ph_2SO$ (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride ($Tf_2O$, 1.4 equiv., 0.106 mmol, 18 μL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 9 (2.0 equiv., 0.15 mmol, 39.0 mg) in 1:1 dichloromethane/dioxane (0.50 mL/0.50 mL). The reaction mixture was then allowed to slowly warm up to room temperature and stirred for 18 h. The reaction was then filtered through Celite and washed twice with saturated aqueous $NaHCO_3$. The organic layer was dried ($Na_2SO_4$), filtered and concentrated. The crude product was purified by silica gel flash column chromatography (20%→30% ethyl acetate in hexanes) to afford product 17 (0.060 mmol, 46.8 mg, 80% yield, α-only), the spectroscopic data of which is in good agreement with those reported previously.[27]

$^1$H NMR (500 MHz, $CDCl_3$): δ 7.36-7.23 (m, 20H), 5.50 (d, J=4.9 Hz, 1H), 5.00 (d, J=3.0 Hz, 1H), 4.93 (d, J=11.4 Hz, 1H), 4.83 (d, J=11.6 Hz, 1H), 4.75-4.71 (m, 3H), 4.59-4.55 (m, 2H), 4.47 (d, J=11.8 Hz, 1H), 4.41 (d, J=11.8 Hz, 1H), 4.32-4.29 (m, 2H), 4.06-3.99 (m, 4H), 3.96-3.94 (m, 1H), 3.80-3.71 (m, 2H), 3.57 (t, J=8.3 Hz, 1H), 3.53-3.49 (m, 1H), 1.51 (s, 3H), 1.42 (s, 3H), 1.32 (s, 3H), 1.29 (s, 3H); $^{13}$C NMR (125 MHz, $CDCl_3$) δ 139.0, 138.8, 138.1, 128.4, 128.3, 128.2, 127.8, 127.7, 127.6, 127.5, 127.4, 109.2, 108.5, 97.6, 96.3, 79.0, 76.5, 75.0, 74.8, 73.4, 73.1, 72.7, 70.9, 70.7, 69.2, 68.7, 66.4, 65.9, 26.2, 26.1, 25.0, 24.6.

74.7, 73.4, 73.3, 72.7, 71.1, 69.8, 69.2, 68.1, 61.7, 55.3; LRMS (ESI, pos. ion) m/z: calcd. for $C_{55}H_{58}O_{11}Na$ (M+Na) 917.39. found 917.27.

Example 9

Methyl-O-(2,3,4,6-tetra-O-benzyl-α-D-glucopyranosyl)-(1→3)-2-O-benzyl-4,6-O-benzylidine-α-D-glucopyranoside (18)

A solution of donor 1a (1.0 equiv., 0.075 mmol, 47.5 mg), $Ph_2SO$ (2.8 equiv., 0.210 mmol, 42.5 mg), TTBP (3.0 equiv., 0.225 mmol, 55.9 mg), N-methylmaleimide (3.0 equiv., 0.225 mmol, 25.0 mg) and freshly activated 4 Å molecular sieves (100 mg) in dry dichloromethane (1.00 mL) was cooled to −78° C. and then treated drop-wise with trifluoromethanesulfonic anhydride ($Tf_2O$, 1.4 equiv., 0.106 mmol, 18 μL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 10 (2.0 equiv., 0.150 mmol, 55.8 mg) in 1:1 dichloromethane/dioxane (0.50 mL/0.50 mL). The reaction mixture was then allowed to slowly warm up to room temperature and stirred for 40 h. The reaction was first filtered through Celite and washed twice with saturated aqueous $NaHCO_3$. The organic layer was dried ($Na_2SO_4$), filtered and concentrated. The crude product was purified by silica gel flash column chromatography (25% ethyl acetate in hexanes) to afford product 18 (0.044 mmol, 39.3 mg, 59% yield, 19:1 α:β), the spectroscopic data of which is in good agreement with those reported previously.[23]

$^1$H NMR (500 MHz, $CDCl_3$): δ 7.69-6.92 (m, 30H), 5.59 (d, J=4.0 Hz, 1H), 5.47 (s, 1H), 4.99 (d, J=10.5 Hz, 1H), 4.80 (dd, J=11.0 Hz, 1H), 4.79 (d, J=11.0 Hz, 1H), 4.71 (d, J=3.5 Hz, 1H), 4.65 (d, J=11.4 Hz, 1H), 4.58 (d, J=12.0 Hz, 1H), 4.57 (d, J=11.5 Hz, 1H), 4.55 (d, J=12.0 Hz, 1H), 4.41 (d, J=11.0 Hz, 1H), 4.38 (t, J=9.5 Hz, 1H), 4.32 (d, J=12.5 Hz, 1H), 4.29 (d, J=12.0 Hz, 1H), 4.24 (dd, J=10.0, 4.5 Hz, 1H), 4.21-4.18 (m, 1H), 3.95 (t, J=9.6 Hz, 1H), 3.89-3.63 (m, 5H), 3.52-3.45 (m, 3H), 3.41 (s, 3H); $^{13}$C NMR (125 MHz, $CDCl_3$) δ 134.0, 138.9, 138.1, 137.8, 137.4, 137.1, 129.4, 128.7, 128.4, 128.3, 128.2, 128.1, 128.0, 127.9, 127.6, 127.5, 127.4, 127.3, 126.4, 102.1, 98.5, 96.1, 82.8, 81.6, 78.7, 78.0, 77.5,

Example 10

Methyl-O-(2,3,4,6-tetra-O-benzyl-α-D-galactopyranosyl)-(1→3)-2-O-benzyl-4,6-O-benzylidine-α-D-glucopyranoside (19)

A solution of donor 1b (1.0 equiv., 0.075 mmol, 47.5 mg), $Ph_2SO$ (2.8 equiv., 0.210 mmol, 42.5 mg), TTBP (3.0 equiv., 0.225 mmol, 55.9 mg), N-methylmaleimide (3.0 equiv., 0.225 mmol, 25.0 mg) and freshly activated 4 Å molecular sieves (100 mg) in dry dichloromethane (1.00 mL) was cooled to −78° C. and then treated drop-wise with trifluoromethanesulfonic anhydride ($Tf_2O$, 1.4 equiv., 0.106 mmol, 18 μL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 10 (2.0 equiv., 0.150 mmol, 55.8 mg) in 1:1 dichloromethane/dioxane (0.50 mL/0.50 mL). The reaction mixture was then allowed to slowly warm up to room temperature and stirred for 40 h. The reaction was then filtered through Celite and washed twice with saturated aqueous $NaHCO_3$. The organic layer was dried ($Na_2SO_4$), filtered and concentrated. The crude product was purified by silica gel flash column chromatography (25% ethyl acetate in hexanes) to afford product 19 (0.052 mmol, 46.6 mg, 70% yield, 20:1 α:β), the spectroscopic data of which is in good agreement with those reported previously.[23]

$^1$H NMR (500 MHz, $CDCl_3$): δ 7.43-7.25 (m, 25H), 7.21-7.17 (m, 1H), 7.14-7.11 (m, 2H), 7.05 (d, J=7.0 Hz, 2H), 5.65 (d, J=3.6 Hz, 1H), 5.47 (s, 1H), 4.92 (d, J=11.3 Hz, 1H), 4.88 (d, J=11.8 Hz, 1H), 4.78-4.74 (m, 2H), 4.62 (d, J=12.4, 1H), 4.58-4.55 (m, 3H), 4.47 (d, J=12.3 Hz, 1H), 4.42-4.37 (m, 3H), 4.36 (d, J=11.7 Hz, 1H), 4.24 (dd, J=5.5, 4.8 Hz, 1H), 4.02 (dd, J=6.4, 3.5 Hz, 1H), 3.99-3.94 (m, 2H), 3.86 (td, J=10.0, 4.7 Hz, 1H), 3.77 (t, J=9.3 Hz, 1H), 3.71 (t, J=10.3 Hz, 1H), 3.66-3.62 (m, 2H), 3.59-3.55 (m, 1H), 3.37 (s, 3H); $^{13}$C NMR (125 MHz, $CDCl_3$) δ 139.0, 138.9, 138.5, 138.4, 138.0, 137.1, 129.2, 128.5, 128.4, 128.3, 128.2, 128.1, 128.0, 127.9, 127.4, 127.3, 127.2, 126.3, 101.8, 98.8, 96.8, 83.0, 78.4, 78.3, 75.8, 75.3, 74.9, 73.5, 73.0, 72.4, 71.7, 69.2, 68.8, 68.5, 61.8, 55.3.

Example 11

Methyl-O-(2,3,4,6-tetra-O-benzyl-α-D-glucopyranosyl-(1→4)-2,3,6-tri-O-benzyl-α-D glucopyranoside (20)

A solution of donor 1a (1.0 equiv., 0.075 mmol, 47.5 mg), Ph$_2$SO (2.8 equiv., 0.210 mmol, 42.5 mg), TTBP (3.0 equiv., 0.225 mmol, 55.9 mg), N-methylmaleimide (3.0 equiv., 0.225 mmol, 25.0 mg) and freshly activated 4 Å molecular sieves (100 mg) in dry dichloromethane (1.00 mL) was cooled to −78° C. and then treated drop-wise with trifluoromethanesulfonic anhydride (Tf$_2$O, 1.4 equiv., 0.105 mmol, 17.6 µL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 11 (2.0 equiv., 0.150 mmol, 69.6 mg) in 1:1 dichloromethane/dioxane (0.50 mL/0.50 mL). The reaction mixture was then allowed to slowly warm up to room temperature and stirred for 64 h. The reaction was then filtered through Celite and washed twice with saturated aqueous NaHCO$_3$. The organic layer was dried (Na$_2$SO$_4$), filtered and concentrated. The crude product was purified by silica gel flash column chromatography (30% ethyl acetate in hexanes) to afford product 20 (0.031 mmol, 30.1 mg, 41% yield, α-only), the spectroscopic data of which is in good agreement with those reported previously.[24]

$^1$H NMR (500 MHz, CDCl$_3$): δ 7.32-7.06 (m, 35H), 5.70 (d, J=3.6 Hz, 1H), 5.04 (d, J=11.5 Hz, 1H), 4.88 (d, J=10.8 Hz, 1H), 4.80 (d, J=11.7 Hz, 1H), 4.78 (d, J=10.6 Hz, 1H), 4.77 (d, J=10.9 Hz, 1H), 4.70 (d, J=12.1 Hz, 1H), 4.60 (d, J=3.6 Hz, 1H), 4.59 (d, J=11.9 Hz, 1H), 4.57 (d, J=12.2 Hz, 1H), 4.54 (d, J=11.9 Hz, 1H), 4.52 (d, J=12.2 Hz, 1H), 4.49 (s, 2H), 4.41 (d, J=10.8 Hz, 1H), 4.27 (d, J=12.1 Hz, 1H), 4.09 (t, J=8.8 Hz, 1H), 4.07 (t, J=9.0 Hz, 1H), 3.90 (dd, J=9.8, 8.6 Hz, 1H), 3.84-3.67 (m, 5H), 3.59 (dd, J=9.2, 3.7 Hz, 1H), 3.49 (dd, J=9.7, 3.6 Hz, 1H), 3.48 (dd, J=10.7, 2.9 Hz, 1H), 3.38 (J=10.7, 1.6 Hz, 1H), 3.37 (s, 3H); $^{13}$C NMR (125 MHz, CDCl$_3$) δ 138.9, 138.8, 138.5, 138.2, 138.0, 137.9, 128.5-126.8, 97.8, 96.7, 82.0, 79.4, 77.8, 76.8, 75.5, 74.9, 74.4, 73.5, 73.3, 73.2, 73.2, 72.6, 70.9, 69.6, 69.1, 68.3, 55.2; LRMS (ESI, pos. ion) m/z: calcd. for C$_{62}$H$_{66}$O$_{11}$ (M+Na) 1009.46. found 1009.28.

Example 12

Phenylthio-(2,3,4,6-tetra-O-benzyl-α-D-glucopyranosyl)-(1->6)-2,3,4-tri-O-benzyl-β-D-glucopyranoside (22)

A solution of donor 1a (1.0 equiv., 0.075 mmol, 47.5 mg), Ph$_2$SO (2.8 equiv., 0.210 mmol, 42.5 mg), TTBP (3.0 equiv., 0.225 mmol, 55.9 mg), N-methylmaleimide (1.5 equiv., 0.113 mmol, 12.5 mg) and freshly activated 4 Å molecular sieves (100 mg) in dry dichloromethane (1.00 mL) was cooled to −78° C. and then treated drop-wise with trifluoromethanesulfonic anhydride (Tf$_2$O, 1.4 equiv., 0.106 mmol, 18 µL). After stirring at low temperature for 5 min, a solution of tetrabutylammonium iodide (TBAI, 5 equiv., 0.375 mmol, 138.0 mg) in dichloromethane (0.75 mL) was added to the reaction. Stirring was continued for an additional 10 min at −78° C., after which the reaction mixture was treated with a solution of acceptor 21 (2.0 equiv., 0.150 mmol, 81.3 mg) in 1:1 dichloromethane/dioxane (0.50 mL/0.50 mL). The reaction mixture was then allowed to slowly warm up to room temperature and stirred for 40 h. The reaction was then filtered through Celite and washed twice with saturated aqueous NaHCO$_3$. The organic layer was dried (Na$_2$SO$_4$), filtered and concentrated. The crude product was purified by silica gel flash column chromatography (20% ethyl acetate in hexanes) to afford product 22 (0.049 mmol, 51.9 mg, 65% yield, 23:1 α:β).

[α]$_D$=+0.15° (c=0.019, CH$_2$Cl$_2$); $^1$H NMR (500 MHz, CDCl$_3$): δ 7.55-7.10 (m, 40H), 5.03 (d, J=3.4 Hz, 1H), 4.98 (d, J=10.8 Hz, 1H), 4.89 (m, 1H), 4.86-4.85 (m, 2H), 4.83-4.79 (m, 3H), 4.77-4.72 (m, 2H), 4.68-4.64 (m, 1H), 4.62 (d, J=6.6 Hz, 1H), 4.59 (d, J=3.3 Hz, 1H), 4.47 (d, J=11 Hz, 1H), 4.43 (d, J=12.2 Hz, 1H), 3.98 (t, J=9.3 Hz, 1H), 3.87-3.83 (m, 2H), 3.79-3.77 (m, 1H), 3.72-3.65 (m, 4H), 3.64-3.57 (m, 3H), 3.49 (dd, J=9.2, 3.5 Hz, 1H), 3.26 (t, J=9.2 Hz, 1H); $^{13}$C NMR (125 MHz, CDCl$_3$) δ 138.9, 138.6, 138.5, 138.2, 138.0, 132.0, 129.0, 128.5, 128.4, 128.3, 128.2, 128.0, 127.9, 127.8, 127.7, 127.6, 127.5, 97.4, 88.1, 86.7, 81.7, 81.1, 80.1, 78.8, 77.7, 77.6, 77.3, 75.6, 75.5, 74.9, 73.4, 72.4, 70.2, 68.6, 66.3, 53.4; LRMS (ESI, pos. ion) m/z: calcd. for C$_{67}$H$_{68}$O$_{10}$S (M+Na) 1087.45. found 1087.45; HRMS (ESI, pos. ion) m/z: calcd. for $C_{67}H_{68}O_{10}S$ (M+Na) 1087.4533. found 1087.4425.

Example 13

23α

Methyl-O-[(2,3,4,6-tetra-O-benzyl-α-D-glucopyranosyl)-(1→6)-2,3,6-tri-O-benzyl-α-D-glucopyranosyl]-(1→6)-2,3,6-tri-O-benzyl-α-D-glucopyranoside (23)

A solution of donor 22 (1.0 equiv., 0.065 mmol, 70.0 mg), Ph₂SO (2.8 equiv., 0.182 mmol, 36.8 mg), TTBP (3.0 equiv., 0.195 mmol, 48.4 mg), N-methylmaleimide (3.0 equiv., 0.195 mmol, 21.7 mg) and freshly activated 4 Å molecular sieves (100 mg) in dry dichloromethane (0.85 mL) was cooled to −78° C. and then treated drop-wise with trifluoromethanesulfonic anhydride (Tf₂O, 1.4 equiv., 0.091 mmol, 15.3 µL). After stirring at low temperature for 5 min, a solution of tetrabutylammonium iodide (TBAI, 5 equiv., 0.325 mmol, 120.0 mg) in dichloromethane (0.65 mL) was added to the reaction. Stirring was continued for an additional 10 min at −78° C., after which the reaction mixture was treated with a solution of acceptor 4 (2.0 equiv., 0.13 mmol, 60.3 mg) in 1:1 dichloromethane/dioxane (0.50 mL/0.50 mL). The reaction mixture was then allowed to slowly warm up to room temperature and stirred for 64 h. The reaction was then filtered through Celite and washed twice with saturated aqueous NaHCO₃. The organic layer was dried (Na₂SO₄), filtered and concentrated. The crude product was purified by silica gel flash column chromatography (25%→30% ethyl acetate in hexanes) to afford product 23 (0.020 mmol, 27.3 mg, 30% yield, 22:1 α:β).

Alternatively, following the addition of acceptor 4 (2.0 equiv., 0.130 mmol, 60.3 mg) at −78° C., the reaction mixture was allowed to slowly warm up to room temperature and then heated to 80° C. under reflux for additional 18 h. After cooling to room temperature, the reaction was filtered through Celite and washed twice with saturated aqueous NaHCO₃. The organic layer was dried (Na₂SO₄), filtered, and concentrated. The crude product was then purified by silica gel flash column chromatography (25%→30% ethyl acetate in hexanes) to afford product 23 (0.027 mmol, 38.2 mg, 42% yield, 14:1 α:β) the spectroscopic data of which is in good agreement with those reported previously.[25]

1H NMR (500 MHz, CDCl₃): δ 7.32-7.10 (m, 50H), 5.01 (d, J=3.3 Hz, 1H), 4.96-4.88 (m, 6H), 4.80 (dd, J=10.7, 2.5 Hz, 2H), 4.75 (d, J=10.9 Hz, 2H), 4.69-4.61 (m, 5H), 4.56-4.52 (m, 5H), 4.44 (d, J=10.9 Hz, 1H), 4.42-4.39 (m, 1H), 3.98-3.92 (m, 3H), 3.81-3.77 (m, 3H), 3.73-3.69 (m, 3H), 3.67-3.59 (m, 5H), 3.53-3.50 (m, 2H), 3.42-3.38 (m, 2H), 3.32 (s, 3H); ¹³C NMR (125 MHz, CDCl₃) 138.8, 138.7, 138.5, 138.5, 138.2, 138.0, 128.4-127.4, 98.0, 97.2, 97.0, 82.1, 81.7, 81.6, 80.3, 80.2, 80.1, 77.8, 77.6, 75.7, 75.5, 75.4, 75.0, 74.9, 74.8, 73.4, 72.3, 72.1, 70.7, 70.5, 70.3, 68.5, 65.8, 55.1; LRMS (ESI, pos. ion) m/z: calcd. for $C_{89}H_{94}O_{16}$ (M+Na) 1442.66. found 1442.28.

REFERENCES CITED

1. R. A. Laine, *Pure Appl. Chem.*, 1997, 69, 1867-1873.
2. (a) A. Varki, *Glycobiology*, 1993, 3, 97-130; (b) C. R. Bertozzi and L. L. Kiessling, *Science*, 2001, 291, 2357-2364; (c) G. W. Hart and R. J. Copeland, *Cell*, 2010, 143, 672-676.
3. (a) R. D. Astronomo and D. R. Burton, *Nat. Rev. Drug Disc.*, 2010, 9, 308-324; (b) Y.-L. Huang and C.-Y. Wu, *Expert Rev. Vaccines*, 2010, 9, 1257-1274; (c) L. Morelli, L. Poletti and L. Lay, *Eur. J Org. Chem.*, 2011, 5723-5777.
4. (a) A. V. Demchenko, *Synlett*, 2003, 1225-1240; (b) X. Zhu and R. R. Schmidt, *Angew Chem. Int. Ed.* 2009, 48, 1900-1934.
5. National Research Council, Committee on Assessing the Importance and Impact of Glycomics and Glycosciences, *Transforming Glycoscience: A Roadmap for the Future*, The National Academies Press, Washington, D.C. 2012.
6. For examples of the use of chiral auxiliaries see: (a) J.-H. Kim, H. Yang and G.-J. Boons, *Angew. Chem. Int. Ed.*, 2005, 44, 947-949; (b) J.-H. Kim, H. Yang, J. Park and G.-J. Boons, *J. Am. Chem. Soc.*, 2005, 127, 12090-12097; (c) M. A. Fascione, S. J. Adshead, S. A. Stalford, C. A. Kilner, A. G. Leach and W. B. Turnbull, *Chem. Commun.*, 2009, 5841-5843; (d) M. A. Fascione and W. B. Turnbull *Bielstein J Org. Chem.*, 2010, 6, 19; (e) T. J. Boltje, J.-H. Kim, J. Park and G.-J. Boons, *Nat. Chem.*, 2010, 2, 552-557; (f) M. A. Fascione, C. A. Kilner, A. G. Leach and W. B. Turnbull, *Chem. Eur. J*, 2012, 18, 321-3331; (g) T. Fang, K.-F. Mo and G.-J. Boons, *J Am. Chem. Soc.*, 2012, 134, 7545-7552.
7. For examples of achiral directing groups see: (a) D. J. Cox and A. J. Fairbanks, *Tetrahedron: Asymmetry*, 2009, 20, 773-780; (b) E. A. Mensah and H. M. Nguyen, *J. Am. Chem. Soc.*, 2009, 131, 8778-8780; (c) E. A. Mensah, F. Yu and H. M. Nguyen, *J. Am. Chem. Soc.*, 40 2010, 132, 14288-14302; (d) J. P. Yasomanee and A. V. Demchenko, *J. Am. Chem. Soc.*, 2012, 134, 20097-20102; (e) A. E. Christina, D. van der Es, J. Dinkelaar, H. S. Overkleeft, G. A. van der Marel and J. D. C. Codee, *Chem. Commun.*, 2012, 48, 2686-2688.
8. For examples of the use of conformation-constraining protecting groups see: (a) D. Crich and W. Cai, *J. Org. Chem.*, 1999, 64, 4926-4930; (b) K. Benakli, C. Zha and R. J. Kerns, *J. Am. Chem. Soc.*, 2001, 123, 9461-9462; (c) T. Zhu and G. J. Boons, *Org. Lett.*, 2001, 3, 4201-4203; (b) R. J. Kerns, C. Zha, K. Benakli and Y.-Z. Liang, *Tetrahedron Lett.*, 2003, 44, 8069-8072; (e) D. Crich, M. de la Mora and A. U. Vinod, *J. Org. Chem.*, 2003, 68, 8142-8148; (f) A. Imamura, H. Ando, S. Korogi, G. Tanabe, O. Muraoka, H. Ishida and M. Kiso, *Tetrahedron Lett.*, 2003, 44, 6725-6728; (g) S. Manabe, K. Ishii and Y. Ito, *J. Am. Chem. Soc.*, 2006, 128, 10666-10667; (h) Y. Geng, Q. Qin and X.-S. Ye, *J. Org. Chem.*, 2012, 77, 5255-5270.

9. For examples of the use of intramolecular aglycone delivery approaches to synthesize a-linked glucopyranosides see: (a) M. Bois, *J. Chem. Soc., Chem. Commun.*, 1992, 913-914; (b) M. Bois, *J. Chem. Soc., Chem. Commun.*, 1993, 791-792; (c) M. Bois and H. C. Hansen, *Chem. Lett.*, 1994, 1049-1052; (d) S. C. Ennis, A. J. Fairbanks, R. J. Tennant-Eyles and H. S. Yeates, *Synlett*, 1999, 1387-1390; (e) S. C. Ennis, A, J. Fairbanks, C. A. Slinn, R, J, Tennant-Eyles and H. S. Yeates, *Tetrahedron*, 2001, 57, 4221-4230; (f) M. Aloui, D. J. Chambers, I. Cumpstey, A. J. Fairbanks, A. J. Redgrave and C. M. P. Seward, *Chem. Eur. J*, 2002, 8, 2608-2621; (g) A. J. Fairbanks, Synlett, 2003, 1945-1958; (h) K. Chayajarus, D. J. Chambers, M. J. Chughtai and A. J. Fairbanks, *Org. Lett.*, 2004, 6, 3797-3800; (i) I. Cumpstey, K. Chayajarus, A. J. Fairbanks, A. J. Redgrave and C. M. P. Seward, *Tetrahedron: Asymmetry*, 2004, 15, 3207-3221; (j) E. Attolino, I Cumpstey and A. J. Fairbanks, *Carbohydr. Res.*, 2006, 341, 1609-1618; (k) A. Ishiwata, Y. Munemura and Y. Ito, *Eur. J. Org. Chem.*, 2008, 4250-4263.

10. For the use of glycosyl sulfonium ions see: (a) A. C. West and C. Schuerch, *J. Am. Chem. Soc.*, 1973, 95, 1333-1335; (b) L. Sun, P. Li and K. Zhao, *Tetrahedron Lett.*, 1994, 35, 7147-7150; (c) J. Park, S. Kawatkar, J.-H. Kim and G.-J. Boons, *Org. Lett.*, 2007, 9, 1959-1962; (d) M. G. Beaver, S. B. Billings and K. A. Woerpel, *J. Am. Chem. Soc.*, 2008, 130, 2082-2086; (e) T. Nokami, A. Shibuya, S. Manabe, Y. Ito and J.-i. Yoshida, *Chem. Eur. J* 2009, 15, 2252-2255; (f) L. K. Mydock, M. N. Kamat and A. V. Demchenko, *Org. Lett.*, 2011, 13, 2928-2931; (g) T. Nokami, Y. Nozaki, Y. Saigusa, A. Shibuya, S. Manabe, Y. Ito and J.-i. Yoshida, *Org. Lett.*, 2011, 13, 1544-1547.

11. Dimethylformamide has also been reported to favor a-selective glycosylation reactions. See: S.-R. Lu, Y.-H. Lai, J.-H. Chen, C.-Y. Liu and K.-K. T. Mong, *Angew Chem. Int. Ed.*, 2011, 50, 7315-7320.

12. (a) F. J. Kronzer and C. Schuerch, *Carbohydr. Res.*, 1974, 34, 71-78; (b) J. Gervay, T. N. Nguyen and M. J. Hadd, *Carbohydr. Res.*, 1997, 300, 119-125; (c) M. J. Hadd and J. Gervay, *Carbohydr. Res.*, 1999, 320, 61-69; (d) S, N. Lam and J. Gervay-Hague, *J. Org. Lett.*, 2002, 4, 90 2039-2042.

13. (a) R. U. Lemieux, K. B. Hendriks, R. V. Stick and K. James, *J. Am. Chem. Soc.*, 1975, 97, 4056-4062; (b) R. U. Lemieux and H. Driguez, *J. Am. Chem. Soc.*, 1975, 97, 4063-4069; (c) R. U. Lemieux and H. Driguez, *J. Am. Chem. Soc.*, 1975, 97, 4069-4075.

14. For examples of iterative oligosaccharide synthesis see ref 8e, 9i, 9k and: (a) R. W. Friesen and S. J. Danishefsky, *J. Am. Chem. Soc.*, 1989, 111, 6656-6660; (b) H. M. Nguyen, J. L. Poole and D. Y. Gin, *Angew. Chem. Int. Ed.*, 2001, 40, 414-417; (c) S. Yamago, T. Yamada, O. Hara, H. Ito, Y. Mino and J.-i. Yoshida, *Org. Lett.*, 2001, 3, 3867-3870; (d) S. Yamago, T. Yamada, T. Maruyama, and J.-i. Yoshida, *Angew. Chem. Int. Ed.*, 2004, 43, 2145-2148.

15. C.-H. Hsu, S.-C. Hung, C.-Y. Wu and C.-H. Wong, *Angew. Chem. Int. Ed.*, 2011, 50, 11872-11923.

16. C.-T. Ren, Y.-H. Tsai, Y.-L. Yang, W. Zou and S.-H. Wu, *J. Org. Chem.*, 2007, 72, 5427-5430.

17. S. Boonyarattanakalin, X. Liu, M. Michieletti, B. Lepenies and P. H. Seeberger, *J. Am. Chem. Soc.*, 2008, 130, 16791-16799.

18. J. Xue and Z. Guo, J., *Carbohydr. Chem.*, 2008, 27, 51-69.

19. M. Matwiejuk and J. Thiem, J., *Eur. J. Org. Chem.*, 2011, 5860-5878.

20. S. Tani, S. Sawadi, M. Kojima, S. Akai and K.-i. Sato, *Tetrahedron Lett.*, 2007, 48, 3101-3104.

21. M. Koshiba, N. Suzuki, R. Arihara, T. Tsuda, H. Nambu, S, Nakamura and S. Hashimoto, *Chem. Asian J.*, 2008, 3, 1664-1677.

22. A. P. Dieskau and B. Plietker, *Org. Lett.*, 2011, 13, 5544-5547.

23. D.-C. Xiong, L.-H. Zhang and X.-S. Ye, *Adv. Synth. Catal.*, 2008, 350, 1696-1700.

24. B. A. Garcia and D. Y. Gin, *J. Am. Chem. Soc.*, 2000, 122, 4269-4279.

25. S. Kaeothip, P. Pornsuriyasak, N. P. Rath and A. V. Demchenko, *Org. Lett.*, 2009, 11, 799-802.

26. H. M. Nguyen, Y. Chen, S. G. Duron and D. Y. Gin, *J. Am. Chem. Soc.*, 2001, 123, 8766-8772.

27. D. J. Cox, M. D. Smith and A. J. Fairbanks, *Org. Lett.*, 2010, 12, 1452-1455.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

INCORPORATION BY REFERENCE

All patents and published patent applications mentioned in the description above are incorporated by reference herein in their entirety.

We claim:

1. A method of forming a glycosidic bond, comprising:
combining a glycosyl phenyl sulfide, phenyl sulfoxide, molecular sieves, and a non-nucleophilic base, thereby forming a first reaction mixture;
combining trifluoromethanesulfonic anhydride and the first reaction mixture, thereby forming a second reaction mixture;
combining tetrabutylammonium iodide (TBAI) and the second reaction mixture, thereby forming a third reaction mixture; and
combining a glycosyl acceptor and the third reaction mixture, thereby forming a glycosidic bond;
wherein the glycosidic bond is formed with greater than or equal to 90% stereoselectivity for an α linkage.

2. The method of claim 1, wherein the glycosidic bond is formed with greater than or equal to 95% stereoselectivity for an α linkage.

3. The method of claim 1, wherein the glycosidic bond is formed with greater than or equal to 98% stereoselectivity for an α linkage.

4. The method of claim 1, wherein the glycosidic bond is formed with greater than or equal to 99% stereoselectivity for an α linkage.

5. The method of claim 1, wherein said molecular sieves are 4 Angstrom molecular sieves.

6. The method of claim 1, wherein the non-nucleophilic base is selected from the group consisting of tri-tert-butylpyrimidine (TTBP), 2,6-di-tert-butylpyridine, N,N-diisopropylethylamine (DIPEA), 1,8-diazabicycloundec-7-ene (DBU), 2,6-lutidine, 2,4,6-collidine, tert-butyl-phosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide.

7. The method of claim 6, wherein the non-nucleophilic base is tri-tert-butylpyrimidine (TTBP).

8. The method of claim 1, wherein the glycosyl phenyl sulfide is selected from the group consisting of

9. The method of claim 1, wherein the glycosyl acceptor comprises an alcohol, a thiol, or an amine.

10. The method of claim 9, wherein the glycosyl acceptor is a monosaccharide, a disaccharide, an oligosaccharide, or a polysaccharide, each comprising at least one —OH, —SH, or primary or secondary amino group.

11. The method of claim 1, wherein the glycosyl acceptor is selected from the group consisting of:

12. The method of claim 1, wherein the first reaction mixture further comprises a thiol scavenger, wherein the thiol scavenger is N-methylmaleimide.

13. The method of claim 1, further comprising the step of cooling the first reaction mixture to about −78° C.

14. The method of claim 1, wherein the TBAI is present in about 5-fold molar excess relative to the glycosyl phenyl sulfide.

* * * * *